United States Patent [19]
Ellenbogen et al.

[11] Patent Number: 5,879,698

[45] Date of Patent: *Mar. 9, 1999

[54] CALCIUM DIETARY SUPPLEMENT

[75] Inventors: Leon Ellenbogen, New York, N.Y.; Lisa C. Buono, Saddle Brook, N.J.

[73] Assignee: American Cyanamid Company, Madison, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 832,079

[22] Filed: Apr. 3, 1997

Related U.S. Application Data

[60] Continuation of Ser. No. 482,998, Jun. 7, 1995, abandoned, which is a division of Ser. No. 312,352, Sep. 26, 1994, abandoned.

[51] Int. Cl.$^6$ ................ A61K 9/68; A61K 9/20; A61K 9/14; A61K 33/34

[52] U.S. Cl. ............ 424/440; 424/451; 424/464; 424/489; 424/630; 424/639; 424/641; 424/657; 424/682

[58] Field of Search ............... 424/440, 630, 424/464, 639, 489, 641, 682, 687, 657, 451

[56] References Cited

U.S. PATENT DOCUMENTS

| | | | |
|---|---|---|---|
| 4,431,634 | 2/1984 | Ellenbogen | 424/147 |
| 4,849,220 | 7/1989 | Nielsen et al. | 424/659 |
| 5,151,274 | 9/1992 | Saltman et al. | 424/630 |

*Primary Examiner*—Thurman K. Page
*Assistant Examiner*—Sharon Howard
*Attorney, Agent, or Firm*—Steven H. Flynn

[57] ABSTRACT

A dietary supplement composition is disclosed which comprises a calcium salt, vitamin D and at least one mineral, preferably a boron compound. Other minerals may be present, in addition to, or instead of the boron compound, such as copper compounds, Magnesium compounds, manganese compounds and zinc compounds.

2 Claims, 1 Drawing Sheet

CALCIUM DIETARY SUPPLEMENT

This application is a continuation of application Ser. No. 08/482,998 filed on Jun. 7, 1995, now abandoned, which is a divisional of application Ser. No. 08/312,352 filed on Sep. 26, 1994, now abandoned.

BACKGROUND AND SUMMARY OF THE INVENTION

Mineral and vitamin compositions are routinely used as dietary supplements either as therapeutic preparations directed to a specific medical problem or as general nutritional supplements.

Calcium and trace mineral supplementation is important for adults as well as growing children. The adult population requires additional calcium to help prevent the bone loss that goes along with the normal aging process. Postmenopausal women require more calcium due to the change in their hormonal status, which can accelerate the bone loss rate leading to osteoporosis.

Osteoporosis is a prevalent condition, affecting as many as 15–20 million individuals in the United States. In osteoporosis, bone mass decreases causing bones to be more brittle, thus bones become more susceptible to fracture. It has been estimated that at least 1.3 million fractures in the U.S. are attributable to this disease [National Osteoporosis Foundation, *Stand UP to Osteoporosis, Your Guide to Staving Healthy and and Independent Through Prevention and Treatment*, Washington, D.C. 1992]. Many scientist believe that a chronic shortage of dietary calcium is one very important factor leading to osteoporosis. Optimal calcium intake (1000–1500 mg) for adults may be achieved through diet, calcium fortified foods, calcium supplements or combinations thereof. Studies show that the usual intake of calcium for adult woment in the U.S. is between 450–500 mg per day [U.S. Department of Health and Human Services, Public Health Service National Institutes of Health, *Osteoporosis. Cause, Treatment Prevention*, Maryland, National Institutes of Health, 1987]; this amount is well below the United States Recommended Daily Allowance (U.S. RDA). It has recently been reported that in addition to calcium, the minerals boron, copper, magnesium, manganese and zinc, play an important role in bone formation [Strause, L., et at: The Role of Trace Elements in Bone Metabolism, *Nutritional Aspects of Osteoporosis*, New York, Raven Press, p. 223–233, 1992 and Nielsen, F.: Facts and Fallacies about Boron, *Nutrition Today*, 27 (3): 6–12, May/June 1992). In addition, vitamin D is known to play a critical role in the absorption of calcium by the human body. The recommended daily intake of vitamin D is between 400 INternational Units, hereinafter called I. U., and 800 I.U. for an elderly person.

The present invention relates to a calcium, vitamin D and multimineral dietary supplement composition. The multiminerals can comprise one or more salts of boron, copper, magnesium, manganese, zinc. The composition also comprises pharmaceutically acceptable carriers and excipients.

DETAILED DESCRIPTION OF THE INVENTION

Figure 1:
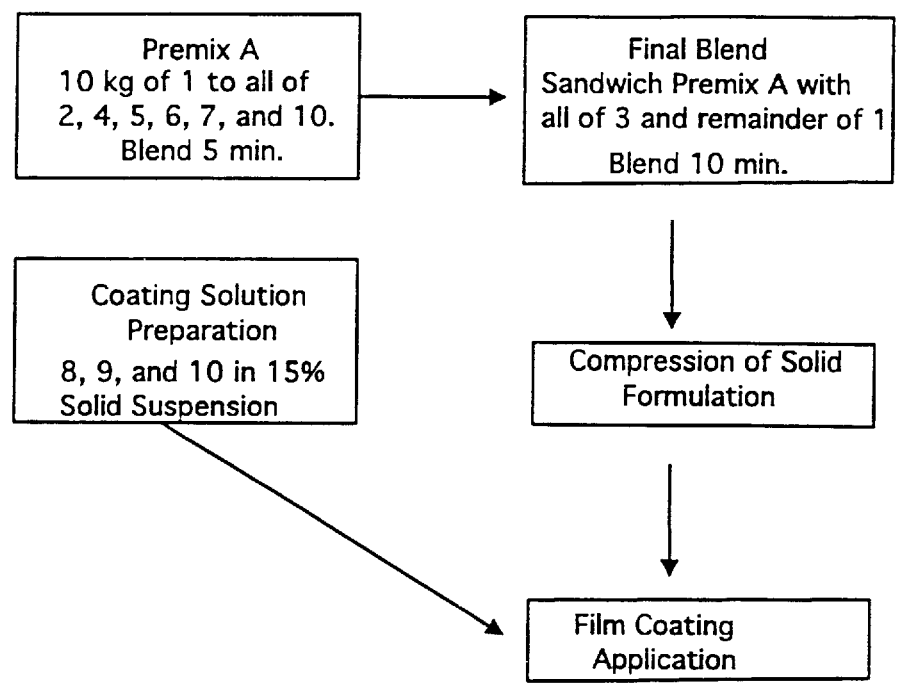
FIG. 1 is a schematic representation of a mode of production of the dietary supplement composition of the present invention as practiced in Example 1.

The present invention relates to a calcium, vitamin D, and multimineral dietary supplement composition to protect against disorders of bone loss.

It is known that not all calcium sources are equal in terms of bioavailability and absorption. The preferred form of calcium is calcium carbonate, which contains the highest amount of absorbable calcium, 40% elemental calcium. Calcium carbonate is cheap, readily available and easily compacted to make a tablet with greater calcium content. Because of the higher elemental calcium content of calcium carbonate, a tablet can be made smaller and can contain a higher concentration of available calcium. Since the tablet can be smaller, it is easier to swallow especially for elderly people.

Other sources of calcium for supplemental use are calcium gluconate, calcium lactate, dibasic calcium phosphate and calcium citrate and the like. Elemental calcium, is supplied in the range of about 400 and 1,000 mg.

Vitamin D, critical in the role of calcium absorption, is added in the range between 50 I. U., and 800 I.U. The preferred range is between 200–400 I.U.

The multiminerals are boron, copper, magnesium, manganese and zinc. The anions for the minerals can be phosphate, chloride, sulfate, nitrate or the like.

Copper, zinc and magnesium are need in bone formation and metabolim. They are essential as cofactors for several enzymes involved in organic bone matrix synthesis. The evidence from human studies demonstrates the metabolic necessity in the formation and maintenance of a healthy skeleton (Strause, L., et at: The Role of Trace Elements in Bone Metabolism, *Nutritional Aspects of Osteoporosis*, New York, Raven Press, p. 223–233, 1992). Manganese deficiency manifests itself in impaired growth and skeletal abnormalities. In addition, magnesium is an essential constituent of all soft tissue and bone. Much of the magnesium in the body is combined with calcium and phosphate in bone (Avioli, L.: Calcium and Osteoporosis, *Ann. Rev. Nutr.*, 4:471–491, 1984). The lack of boron effects the composition, structure and strength of bone. The effect of boron on bone metabolism might reflect its known action on macromineral metabolism. Studies in humans strongly suggest that boron is beneficial to calcium metabolism and absorption (Nielsen, F.: Facts and Fallacies about Boron, *Nutrition Today*, 27 (3): 6–12, May/June 1992).

The preferred amounts of the mineral supplements are:

boron salt from 50 to 3,000 micrograms;

copper salt from 0.10 to 5.0 mg;

magnesium salt from 10 to 150 mg;

manganese salt from 3 to 10 mg; and zinc salt from 3 to 25 mg.

As a general statement, the total weight of the dosage form is less than about 3.0 g. In the preferred embodiment the dosage form is equal to or less that about 2.0 g.

The present formulation may also include preservatives such as benzoic acid and salts thereof, butylated hydroxyanisole, butylated hydroxytoluene, sulfur dioxide and the like; food grade emulsifiers such as lecithin, mono- and diglycerides of long chain fatty acids, and propylene glycol esters; and pharmaceutically acceptable carriers and excipients, which are known to those skilled in the art.

As used herein, pharmaceutically acceptable is a component which is suitable for used in humans without undue adverse side effects, such as irritation, toxicity, and allergic response.

The present formulation may be in oral solid dosage form for example a tablet, capsule, lozenger, chewable tablet or bulk powder. The tablet, capsule or lozenger may contain suitable binders, lubricants, diluents, disintegrating agents, coloring agents, flavoring agents, flow-inducing agents and melting agents which are known to those skilled in the art.

The present formulation may also be in a liquid dosage form which includes an emulsion and suspension. The liquid dosage form may contain, for example, suitable solvents, preservatives, emulsifying agents, suspending agents, diluents, sweeteners, melting agents, and coloring and flavoring agents, which are known to skilled in the art.

It is preferred to administer the composition of the present invention in the form of tablets; however, any form of oral administration can be used.

The solid dosage form may have a film coating to protect the ingredients from moisture, oxygen or light and to mask any undesirable taste or appearance. Suitable coating agents include cellulose, hydroxypropylmethylcellulose, cellulose phthalate, methacryulic copolymer and shellac. An enteric coating may be employed, as well as coloring agents for identification, and if desired, the solid form may be polished with a waxy composition, such as carnuba wax.

The following example is for illustrative purposes and is not to be construed as limiting the invention. All parts are by weight unless otherwise specified.

EXAMPLE 1

As shown in FIG. 1, a mixture of calcium carbonate, pharmaceutical grade with malto-dextrin BTH granulation; Vitamin D3 CSW, Cold Water Soluble, 100,000 I. U./g; cupric oxide, magnesium oxide, manganese sulfate, sodium borate.10 $H_2O$ and sodium lauryl sulfate is blended for 5 minutes (Premix A).

Premix A is sandwiched with zinc oxide and the remainder of the calcium carbonate and blended for 10 minutes (Final Blend).

A 15% solid suspension coating is prepared by mixing pink film (Dusty Rose) coating premix, mineral oil, and sodium lauryl sulfate (Coating Solution Preparation).

The Final Blend is compressed into the desired dosage form.

The Coating Solution Preparation is applied to the solid dosage.

Listed below are the individual quantities of the ingredients preferred for the calcium, vitamin D, and multimineral dietary supplement formulation.

| Raw Material | Label Claim per Dosage | Quantity of Raw Material per Dosage (g) |
|---|---|---|
| 1. Calcium carbonate pharmaceutical grade w/maltodextrin BTH granulation | 600 mg Ca++ | 1.690000 |
| 2. Vitamin D3 CWS 100,000 I.U./g | 200 IU/D | 0.002800 |
| 3. Zinc Oxide | 7.5 mg Zn | 0.009335 |
| 4. Cupric Oxide | 1.0 mg Cu | 0.001252 |
| 5. Magnesium Oxide | 40 mg Mg | 0.066313 |
| 6. Manganese Sulfate | 1.8 mg Mn | 0.005540 |
| 7. Sodium Borate · 10 $H_2O$ | 250 mcg B | 0.002230 |
| 8. Pink Film (Dusty Rose) Coating Premix | | 0.025900 |
| 9. Mineral Oil | | 0.007350 |
| 10. Sodium Lauryl Sulfate | | 0.001750 |
| Total Table Weight | | 1.812470 |

The numbers shown in FIG. 1 correspond to the raw material numbers above.

We claim:

1. A dietary supplement composition to protect against bone loss comprising:

a calcium salt having a content of about 1000 to 2500 mg mg;

vitamin D having a content of about 50 to 800 I. U.;

a boron salt content of about 50 to 3,000 micrograms;

a copper salt content of about 0.1 to 5.0 mg;

a magnesium salt content of about 10 to 150 mg;

a manganese salt content of about 3 to 10 mg; and a zinc salt content of about 3 to 25 mg.

2. The composition of claim 1 in an oral dosage form selected from a tablet, a capsule, a lozenger, a chewable tablet and a bulk powder.

* * * * *